US006391653B1

(12) United States Patent
Letcher et al.

(10) Patent No.: US 6,391,653 B1
(45) Date of Patent: May 21, 2002

(54) ACOUSTIC STANDING-WAVE ENHANCEMENT OF A FIBER-OPTIC SALMONELLA BIOSENSOR

(75) Inventors: Stephen V. Letcher; A. Garth Rand, both of Kingston, RI (US); Chonghua Zhou, Ellicott City, MD (US)

(73) Assignee: The Board of Governors for Higher Education, State of Rhode Island and Providence Plantations, Providence, RI (US)

( * ) Notice: Subject to any disclaimer, the term of this patent is extended or adjusted under 35 U.S.C. 154(b) by 0 days.

(21) Appl. No.: 09/619,230

(22) Filed: Jul. 19, 2000

Related U.S. Application Data

(62) Division of application No. 09/020,434, filed on Feb. 9, 1998.

(51) Int. Cl.$^7$ .............................................. G01N 33/543

(52) U.S. Cl. .......................... 436/518; 385/12; 435/7.2; 435/7.32; 435/7.35; 435/287.1; 435/287.2; 435/288.7; 435/808; 436/164; 436/165; 436/172; 436/524; 436/527; 436/805; 422/55; 422/57; 422/58; 422/82.05; 422/82.08; 422/82.11

(58) Field of Search ................................ 435/7.2, 7.32, 435/7.35, 287.1, 287.2, 288.7, 808; 436/164, 165, 172, 518, 524, 527, 805; 422/55, 57, 58, 82.05, 82.08, 82.11; 385/12

(56) References Cited

U.S. PATENT DOCUMENTS

| | | | | |
|---|---|---|---|---|
| 4,558,014 A | * | 12/1985 | Hirschfeld et al. | 436/527 |
| 4,608,344 A | * | 8/1986 | Carter et al. | 436/34 |
| 5,082,630 A | * | 1/1992 | Partin et al. | 422/83 |

* cited by examiner

*Primary Examiner*—Christopher L. Chin
(74) *Attorney, Agent, or Firm*—Samuels, Gauthier & Stevens

(57) ABSTRACT

A fluorescent fiber-optic biosensor system using ultrasonic concentration of particles and cells for the detection of *Salmonella typhimurium*. A biosensor test chamber serves as an ultrasonic standing-wave cell that allows microspheres or cells to be concentrated in parallel layers or in a column along the axis of the cell. A fiber probe along the axis delivers laser excitation to fluorescent-labeled antibodies of Salmonella and collects the fluorescent signal. The Salmonella-antibody complexes are moved acoustically to the axis of the cell, increasing the fluorescent signal. Alternatively, the Salmonella-labelled antibody complexes attach to unlabeled antibodies that have been immobilized on the surface of polystyrene microspheres. This entire structure can be manipulated acoustically and the increase in the fluorescent signal, which can be an order of magnitude, indicates the presence of Salmonella.

5 Claims, 3 Drawing Sheets

ACOUSTIC STANDING-WAVE ENHANCEMENT OF A FIBER-OPTIC SALMONELLA BIOSENSOR

CROSS-REFERENCE TO RELATED APPLICATIONS

This is a division of U.S. application No. 09/020,434 filed Feb. 9, 1998.

GRANT INFORMATION

This work was supported, in part, by the U.S. Department of Agriculture (NRICGP Grant No. 93-37201-9197) and by the URI Partnership for Sensors and Surface Technology. This is contribution number 3435 of the Rhode Island Agricultural Experiment Station.

BACKGROUND OF THE INVENTION

1. Field of the Invention

A fiber-optic biosensor detects pathogens based on immunoassay. Acoustic Enhancement concentrates the bound antibody enhancing detection.

2. Description of the Relevant Art

Sensitive detection of fluorescence or luminescence from biological reaction in vivo is important for many biosensor applications. Considerable effect has been devoted to the development of fiber-optic fluorescent biosensors because of their potential sensitivity, detection speed, and applicability to a wide variety of assay conditions.

Fiber-optic fluorescent immunosensors require that the dye molecules, which indicate unambiguously the presence of the antigen, find their way to the optically active region of the fiber. This can be accomplished by immobilizing the capture antibodies directly on the tip or the tapered core of the fiber, but this means that the capture process is localized and that several rinsing steps are needed to avoid ambiguity and to recycle the system for another measurement. On the other hand, performing the immunoassay on microparticles that are distributed throughout the sample cell and that are subsequently concentrated into the fiber's sensing volume promises greatly improved efficiency. Two well-studied techniques for manipulating microparticles that could be used for this purpose are based on magnetism and n acoustics. The present invention is based in part of the latter technique.

It has long been known that small particles and biological cells suspended in a liquid can be trapped in the force field generated by a stationary ultrasonic wave. The acoustic radiation force on a rigid sphere or on a compliant sphere has been studied by many authors, Chen, X. and Apfel, R. E., *Radiation force on a spherical object in an axisymmetric wave field and its application to the calibration of high-frequency transducers*, J. Acoust. Soc. Am, 99, 1996, 713–724; and Wu, J. and Du, G., *Acoustic radiation force on a small compressible sphere in a focused beam*, J. Acoust. Soc. Am. 87, 1990, 997–1003. It is known that the average force that acts on a small compressive particle as a function of the mean square fluctuation of the pressure and velocity at the point where the particle is located. The results have been applied in many biological applications, such as rapid agglutination testing; Grundy, M. A., Moore, K. and Coakley, W. T., *Increased sensitivity of diagnostic latex agglutination tests in an ultrasonic standing wave field*, J. Immunological Methods, 176, 1994, 169–177; determination of the properties of red blood cells; Weiser, M. A. H. and Apfel, R. E., *Extension of acoustic levitation to include the study of micron-size particles in a more compressible host liquid*, J. Acoust. Soc. Am., 71, 1982, 1261–1268; and the concentration and separation of particles and cells; Whitworth, Glenn and Coakley, W. T., *Particle column formation in a stationary ultrasonic field*, J. Acoust. Soc. Am., 91, 1992, 79–85; and Coakley, W. T., Whitworth, G., Grundy, M. A., Gould, R. K. and Allman, R., *Ultrasonic manipulation of particles and cells*, Bioseparation, 4, 1994, 73–83; and Yasua, K., Kiyama, M. and Umemura, S. *Deoxyribonucleic acid concentration using acoustic radiation force*, J. Acoust. Soc. Am., 99, 1992, 1248–1258. Ultrasonic radiation forces have provided a real-time, non-contact method to manipulate particles and cells.

In a plane standing wave, the particles that are stiffer and/or denser than the surrounding medium gather in the nodal planes spaced one-half wavelength apart. For a standing plane wave confined to a cylindrical container with a rigid wall, if the cross-sectional profile of the sound field has a Besell or Gaussian shape intense on the axis, weak at the wall, then the potential energy of a suspended particle has a gradient in the radial direction. For particles denser than the fluid ($\rho o > \rho$), the force pushes them toward the axis, forming a striated column. For the formation of both layers and columns of particles, the forces are proportional to the acoustic intensity, suggesting improved results with increased sound amplitude and frequency. The intensity is limited, however, by the generation of cavitation and streaming, which destroy the formations.

SUMMARY OF THE INVENTION

Broadly the invention embodies acoustic complex manipulation for enhancement of the sensitivity of a fiber-optic biosensor using fluorescent immunoassay techniques for the rapid detection of a pathogen, e.g. Salmonella. In a preferred embodiment, a fiber-optic probe defines an axis in an acoustic chamber whereby the target complexes are first be formed in parallel layers perpendicular to the fiber and then are concentrated along the fiber for maximum sensitivity.

According to the teachings of the invention various immunoassays can be performed. One embodiment of the invention is a "sandwich" assay in which the Salmonella cells are captured by antibodies that are attached to polystyrene microspheres. The Salmonella is made visible when it captures, in turn, free antibodies that have been labeled with a fluorescent dye. The entire microsphere-antibody-Salmonella-antibody complex is manipulated acoustically.

In another embodiment of the invention, simple Salmonella-antibody complexes are directly concentrated acoustically along the cell axis.

DESCRIPTION OF THE PREFERRED EMBODIMENT(S)

Fiber-Optic Fluorescence Detection System

Figure 1A:
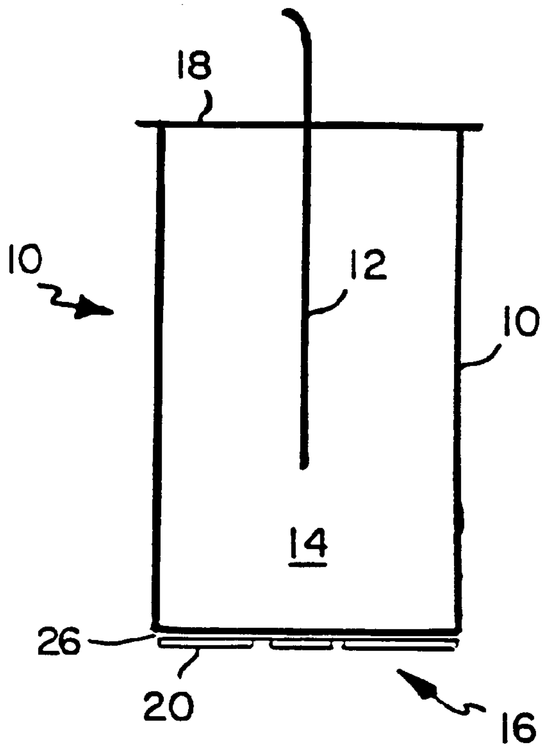
FIGS. 1*a* and 1*b* are front and bottom schematics of an acoustic test chamber.
Figure 1B:
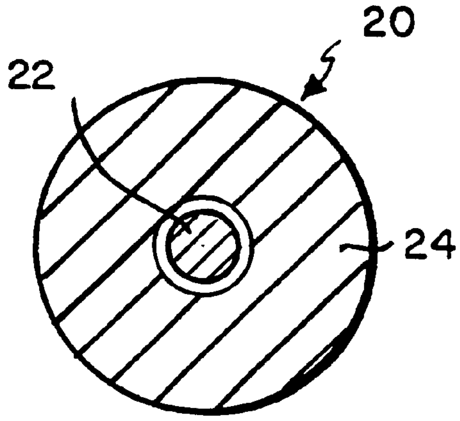

Referring to FIG. 1, a cylindrical test cell 10 is shown with a fiber tip 12 inserted into media 14 in the cell 10. A transducer 16 is located at the bottom of the cell and a reflecting plate 18 is located at the top of the cell. A single step-tapered fiber 12 is used for excitation and detection. The sensing fiber is located along the axis of the cell. The electrode plating of the transducer is indicated. The beam is from a diode laser (λ=650 nm) focused into one branch of a 300-μm 2×2 coupler, one branch of which is connected to the sensing fiber. The sensing fiber is fused silica with a 300-μm core diameter, obtained from 3M Corp. The tip of the sensing fiber 10, which has had its cladding removed and its core diameter reduced in three steps from 300 to 40 μm over a length of 20 mm, is inserted into a test cell 12. The tip and fiber optic sensing system are described in detail in our co-pending application Ser. No. 08/980,653 filed Dec. 1, 1997 which application is incorporated by reference in its entirety into this disclosure.

The laser beam enters the fluid through the stepped faces and excited dye molecules located close to the fiber. A small fraction of the subsequent fluorescent signal re-enters the fiber, passes through two long-pass interference filters and is focused into a fiber that leads to the detecting spectrometer.

Salmonella, Antibodies and Microspheres

*Salmonella typhimurium* samples were obtained from the American Type Culture Collection (Rockville, Md., ATCC 13311). Nutrient broth and nutrient agar from Difco Laboratories (Detroit, Mich.) were used as media for all microbial growth and late counts. Salmonella typhimurium cultures were stored at −80° C. until needed. The cultures were thawed, mixed and two to three loops were used to inoculate 10 ml of nutrient broth. The inoculated broth was incubated until the organisms reached a stationary growth phase (37° C. for 12 hours). The fresh culture was cooled and the organisms were diluted into sterile nutrient broth. The diluted cultures were kept at 4° C. until analyzed. The solutions were prepared with Salmonella concentrations of $2.76\times10^7$, $2.76\times10^6$, and $2.76\times10^5$ colony-forming units per milliliter (CFU/ml).

Purified (>95% IgG) polyclonal Salmonella antibody was obtained from Biodesign International (Kennebunk, Me.). Some of the antibody sample was labeled with the fluorescent dye Cy5, obtained from Biological Detection System, Inc. (Pittsburght Pa.). This dye has an excitation wavelength of 650 nm and the peak of its fluorescence band is at 680 nm.

Some of the unlabeled antibody was immobilized on polystyrene microspheres, obtained from Polysciences, Inc. (Warrington, Pa.), that had an average diameter of 10.6 μm. The immobilization procedure, following suggestions from the manufacturer, was a physical adsorption in a 0.5M carbonate buffer, pH 9.5. The uncreated binding sites were blocked with a 2% bovine serum albumin solution in phosphate-buffered saline (PBS).

Acoustic cells

Referring to FIG. 1, a high-voltage rear electrode of the transducer 16 is divided into two elements: a center electrode 22 and a concentric ring electrode 24. A front electrode 26 acoustically communicates with the bottom of the cell 10. When the two elements are electrically connected and actuated the transducer acts like an ordinary piston transducer whose signal extends over the entire crosg-section of the tube. When only the center electrode is actuated the transducer generates a beam with an approximately Gaussian profile.

Two different sizes of cells were tested to determine if the cell diameter is an important factor of the invention. Cell A consisted of a 10-mm diameter piezoelectric transducer with a fundamental frequency of 3.0 MHz and a polycarbonate tube with an inner diameter of 10 mm and a length of 65 mm. The rear electrode 20 of the transducer 16 was divided into a center spot electrode 22 with radius 1.5 mm and a concentric ring electrode 24 with inner radius 2.5 mm and out radius 5 mm. Cell B was similar to A, but with a length of 50 mm and with a 32-mm inner diameter. The diameter and electrode dimensions of the transducer were scaled accordingly and the resonance frequency was 1.0-MHz. Both cells were terminated with the metal reflecting plate 18 that had a small hole in the center that allowed a 300-μm diameter sensing fiber to define the axis of the tube. The transducers were driven by a Tektronix™ 506 function generator and an ENI (Rochester, N.Y.) power amplifier.

Acoustic Manipulation of Microspheres

To test particle manipulation in each cell, a dilute solution (enough to be visible) of uniformly distributed microspheres was used.

Figure 2:
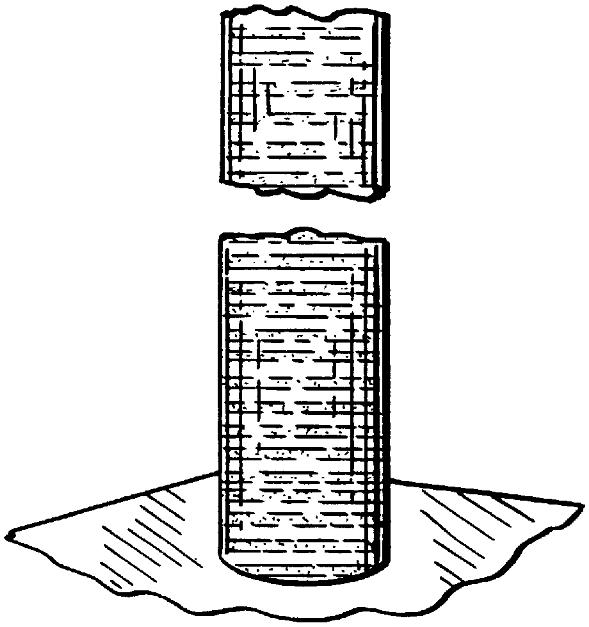
FIG. 2 illustrations uniform parallel layers formed using polystyrene microspheres.
Figure 3:
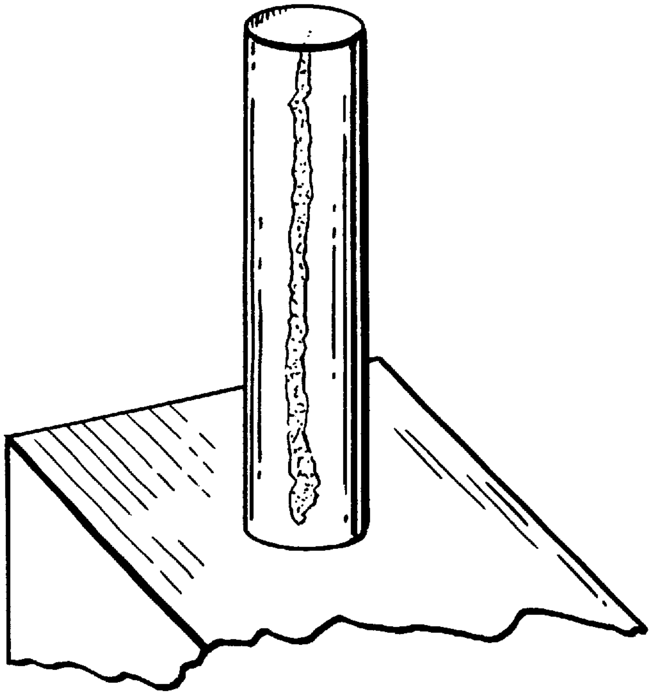
FIG. 3 illustrates column formation of polystyrene particles along a tube axis.

For Cell A, 3.0 MHz transducer, with both electrodes active, the threshold voltage for layer formation was 1 V and the layers, shown in FIG. 2, were uniform and stable throughout the test cell up to 33 V. The layers were not totally destroyed until about 70 V. When the outer electrode was turned off and the center electrode generated the (0,1) acoustic mode, the particles moved toward the axis in about a minute and a stable column was formed along the axis as shown in FIG. 3.

When both the inner and outer electrodes of cell B, operating at 1.0 MHz, were active, it was found that the threshold for layer formation of microspheres was about 4 V (peak-to-peak voltage of signal applied to the transducer-used only for comparison purposes). The layers became sharper with increasing drive voltage until about 20 V, where cavitation destroyed them. At 6 V, the layers were clear and stable. When the outer electrode was disconnected and only the center electrode was active to generate the (0,1) acoustic mode, the layers were destroyed by streaming even at low voltages. The large diameter provided ample counterflow opportunities and easy streaming generation; therefore, a cell with a smaller inner diameter was needed. Also, since both the cavitation threshold and the radiation force are increasing functions of the frequency, a higher frequency was indicated for this application.

When only the center electrode was active from the beginning, layer formation of polystyrene microspheres was limited to a small range around the axis of the cell and, after a few minutes, the layers concentrated at the axis and a column formed, but the column appeared much weaker than when this was preceded by full transducer excitation. Later fluorescence measurement showed that the signal was about 30% smaller than when the column formation was preceded by full-transducer excitation of layers.

Salmonella Immunoassay Using Polystyrene Microspheres

In preparation for the immunoassays, the optical fiber was inserted through the hole in the reflecting plate. It was found that insertion of the fiber did not disturb the formation of layers or columns of microspheres. Even when the fiber was moved around laterally inside the tube, the layers and columns remained stable.

Figure 4:
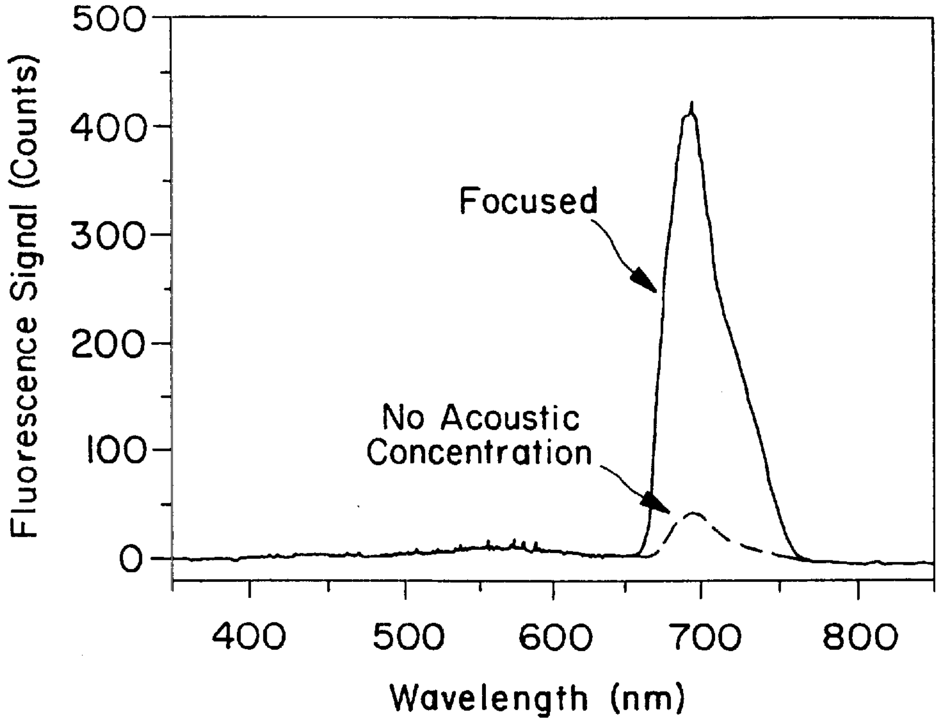
FIG. 4 is a graph of fluorescence spectra with and without acoustic focusing.

The immunoassay test using polystyrene microspheres was performed as follows. Cell A had a volume of 5.1 ml and was about one-third filled with PBS. Then 0.4 ml of 0.25% w/v concentration of microspheres upon which Salmonella antibodies had been immobilized and 1 ml of 0.1 mg/ml concentration of Cy5-labeled antibodies were added. Finally, 2 ml of Salmonella sample was added to the cell and incubated for half an hour. The solution was stirred and additional PBS was added to fill the cell. With the nd plate and the optical fiber in place, the spectrum was measured without acoustic focusing. Then both the outer and inner electrodes were activated and parallel layers formed in less than one second. The outer electrode was then turned off and a column along the axis stabilized in tens of seconds. When the column formed, the fluorescence peak from the fiber spectrometer increased significantly, typically by an order of magnitude, depending on the concentration of Salmonella. FIG. 4 shows the fluorescence spectrum for this complex with a Salmonella concentration of $1.79 \times 10^6$ CFU/ml.

Acoustic focusing results in about an eight-fold increase in the peak value of the spectrum. Without Salmonella, with and without ultrasound, the spectra are unchanged and are comparable to the smaller curve in FIG. 4, suggesting that the smaller curve represents the signal from dy molecules distributed uniformly throughout the cell and that the dye-labeled antibodies do not respond noticeably the acoustic forces.

Figure 5:
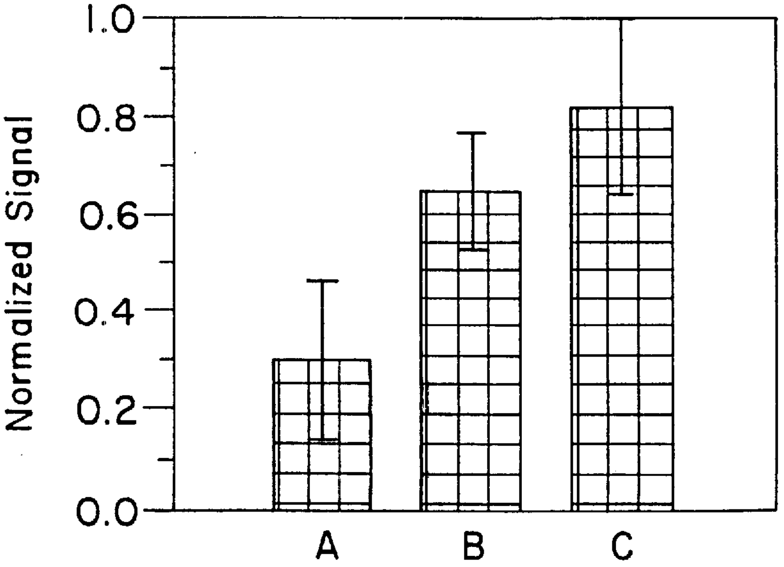
FIG. 5 is a bar graph of fluorescence signal intensities for different Salmonella concentration solutions.

Samples with three different concentrations of Salmonella were tested. The fluorescent signal intensities vs. Salmonella concentration are shown in FIG. 5. The concentrations are $2.76 \times 10^5$ CFU/ml, $2.76 \times 10^6$ CFU/ml, and $2.76 \times 10^7$ CFU/ml for A, B and C respectively. The normalized signal is proportional to the area under the spectral curve. The means and standard deviations of three replicates are shown. It can be seen that the fluorescence response increased with concentration. The normalized signal is proportional to the area under the spectral curve after the ambient light background (without dye molecules) was subtracted. The values in each case are the results of three separate trials. The error bars are due mainly to variations in the details of the structure of the column of particles. The spectrum with a uniform distribution of dye molecules, but without acoustic focusing (smaller curve of FIG. 4) has a normalized signal value of less than 0.1 with an estimated error bar of less than ±5%.

Ultrasound has been used fairly widely to manipulate biological cells directly but, since the radiation forces for formation of layers and columns are proportional to $R^3(\rho o-\rho)$, the effect is much weaker for Salmonella cells than for polystyrene microspheres, which are much larger and somewhat denser. A brief study was made to determine whether ultrasound could concentrate Salmonella cells in this sensor application. Acoustic cell A, described above, was used and fluorescent dye was applied to render the effect visible. The Cy5 dye cannot label the cells directly, so it was first used to label Salmonella by incubating two milliliters of $2.76 \times 10^7$ CFU/ml Salmonella solution with 2 ml of 0.1 mg/ml Cy5-labeled antibody for half an hour. PBS was added to fill the cell.

When the sound was turned on with both electrodes activated, light blue parallel layers could be observed, not nearly as distinct as with microspheres, but still visible. When the outer electrode was turned off, multiple light blue columns could be observed and one column along the axis could be formed with an optimal dried voltage. An increase in the fluorescent signal from the fiber probe along the axis of the cell could also be detected. To assure that the effect was due to the Salmonella cells, a similar test was made with a solution of labeled antibodies alone, which resulted in no visible layer or column formation and no change in is the fluorescent signal received by the fiber.

The threshold drive voltage for layer formation of Salmonella was much higher (10 V) than that for polystyrene spheres and the layers were more vulnerable to acoustic streaming. Furthermore, they could be destroyed by slight variations of the acoustic drive voltage. After the ultrasound procedure, small flocculent clusters could be found in the sample solution. Layer formation on repeated application of sound also became much weaker, suggesting that the Salmonella cells were being aggregated in the sound field.

Fluorescent dye molecules that are not directly involved in the sandwich assay do not, in general, confuse the signal and need not be washed away. A two-step acoustic process was found to be most efficient; first, a full-piston excitation formed particle layers throughout the cell and then these particles were concentrated along the axis of the cell with a Gaussian-profile excitation. It was found that because acoustic streaming or cavitation can destroy the formation of layers and columns, the acoustic frequency and cell dimensions need to be configured for efficient and stable operation. Insertion of an optical fiber along the axis of the cell did not noticeably affect the ultrasonic field or the formation of particle columns. An assay using the ultrasonic manipulation of Salmonella cells themselves is shown to be possible, but is much less efficient and reliable than when aided by the presence of polystyrene microspheres.

The foregoing description has been limited to a specific embodiment of the invention. It will be apparent, however, that variations and modifications can be made to the invention, with the attainment of some or all of the advantages of the invention. Therefore, it is the object of the appended claims to cover all such variations and modifications as come within the true spirit and scope of the invention.

Having described our invention, what we now claim is:

1. A method for the detection of pathogens based on antigen antibody fluorescent complexes which are formed when antigens of the pathogens bind to antibodies labeled with fluorescent molecules dispersed in media using an optical fiber disposed in the media and defining a fiber axis therein which method comprises:

forming the complexes in layers parallel to the fiber axis;

concentrating the complexes in a column along the fiber axis; and sensing the presence of the complexes.

2. The method of claim 1 which comprises:

forming the parallel layers acoustically.

3. The method of claim 2 which comprises:

concentrating the complexes in a column acoustically.

4. The method of claim 1 wherein the complexes further comprise polystyrene microspheres having an antibody that captures the pathogen.

5. The method of claims 1, 2, or 4 wherein the pathogen is selected from the group consisting of Salmonella.

* * * * *